United States Patent
Jensen et al.

(10) Patent No.: US 11,445,974 B2
(45) Date of Patent: Sep. 20, 2022

(54) SYSTEM AND METHOD FOR ADJUSTING THE BLOOD GLUCOSE LEVEL OF A PERSON

(71) Applicant: T&W Engineering A/S, Lynge (DK)

(72) Inventors: Rasmus Stig Jensen, Birkerod (DK); Richard Topholm, Holte (DK); Erik Skov Christensen, Hillerod (DK); Rasmus Elsborg Madsen, Charlottenlund (DK)

(73) Assignee: T&W Engineering A/S, Lynge (DK)

( * ) Notice: Subject to any disclaimer, the term of this patent is extended or adjusted under 35 U.S.C. 154(b) by 0 days.

(21) Appl. No.: 15/653,067

(22) Filed: Jul. 18, 2017

(65) Prior Publication Data
US 2017/0311881 A1 Nov. 2, 2017

Related U.S. Application Data (63) Continuation-in-part of application No. PCT/EP2015/050855, filed on Jan. 19, 2015.

(51) Int. Cl.
*A61B 5/00* (2006.01)
*A61M 5/172* (2006.01)
(Continued)

(52) U.S. Cl.
CPC ........ *A61B 5/4839* (2013.01); *A61B 5/14532* (2013.01); *A61B 5/157* (2013.01);
(Continued)

(58) Field of Classification Search
CPC ............... A61M 5/4839; A61M 5/142; A61M 5/14244; A61B 5/4839; A61B 5/0476; A61B 5/14532
See application file for complete search history.

(56) References Cited

U.S. PATENT DOCUMENTS 6,572,542 B1 * 6/2003 Houben ............... G16H 40/67
                                                       600/300
8,019,410 B1 * 9/2011 Bharmi ............... A61B 5/0205
                                                       600/365
(Continued)

FOREIGN PATENT DOCUMENTS

JP 2007307359 A 11/2007
JP 2013517856 A 5/2013
(Continued)

OTHER PUBLICATIONS

Communication dated Jul. 3, 2018 from the Japanese Patent Office in counterpart application No. 2017-537476.
(Continued)

*Primary Examiner* — Nathan R Price
*Assistant Examiner* — Melissa A Snyder
(74) *Attorney, Agent, or Firm* — Sughrue Mion, PLLC (57) ABSTRACT

A system for adjusting blood glucose level including an insulin delivery device configured to release insulin into the body of a person, and an EEG monitor having an EEG sensing part including EEG electrodes. The EEG monitor can be arranged in the ear region of the person with the EEG sensing part arranged subcutaneously at the scalp or arranged in the ear canal. The EEG monitor includes an EEG signal processor arranged at the ear and adapted for identifying onset of hypoglycemia. The system further includes a wireless link between the EEG monitor and the insulin delivery device. The EEG monitor is configured to submit a warning signal to the insulin delivery device if an upcoming onset of hypoglycemia is identified. The warning message will cause the insulin delivery device to restrict insulin delivery for a predetermined time, and a warning is provided to the person or to a caregiver.

21 Claims, 3 Drawing Sheets

(51) Int. Cl.
  *A61B 5/145* (2006.01)
  *A61M 5/142* (2006.01)
  *A61B 5/15* (2006.01)
  *A61B 5/157* (2006.01)
  *A61B 5/291* (2021.01)
  *A61B 5/369* (2021.01)
  *A61B 5/155* (2006.01)

(52) U.S. Cl.
  CPC .... *A61B 5/150022* (2013.01); *A61B 5/15087* (2013.01); *A61B 5/291* (2021.01); *A61B 5/369* (2021.01); *A61B 5/6814* (2013.01); *A61B 5/6817* (2013.01); *A61B 5/7405* (2013.01); *A61B 5/746* (2013.01); *A61M 5/142* (2013.01); *A61M 5/14244* (2013.01); *A61M 5/1723* (2013.01); *A61B 5/155* (2013.01); *A61B 5/150877* (2013.01); *A61M 5/14276* (2013.01); *A61M 2202/0486* (2013.01); *A61M 2205/18* (2013.01); *A61M 2205/3569* (2013.01); *A61M 2205/581* (2013.01); *A61M 2230/10* (2013.01); *A61M 2230/201* (2013.01)

(56) References Cited

U.S. PATENT DOCUMENTS

| | | | | |
|---|---|---|---|---|
| 8,257,300 | B2* | 9/2012 | Budiman | A61B 5/4839 604/66 |
| 2007/0233051 | A1 | 10/2007 | Hohl et al. | |
| 2010/0057042 | A1* | 3/2010 | Hayter | A61B 5/7275 604/504 |
| 2010/0292634 | A1* | 11/2010 | Kircher, Jr | A61B 5/14532 604/66 |
| 2011/0118578 | A1 | 5/2011 | Timmerman | |
| 2012/0302858 | A1* | 11/2012 | Kidmose | A61B 5/6817 600/379 |
| 2014/0107607 | A1* | 4/2014 | Estes | A61M 5/1452 604/500 |
| 2014/0221966 | A1 | 8/2014 | Buckingham et al. | |
| 2014/0278123 | A1 | 9/2014 | Prodhom et al. | |

FOREIGN PATENT DOCUMENTS

| | | |
|---|---|---|
| WO | 2007144307 A2 | 12/2007 |
| WO | 2009090110 A1 | 7/2009 |
| WO | 2010149158 A1 | 12/2010 |
| WO | 2011091856 A1 | 8/2011 |
| WO | 2012/069549 A1 | 5/2012 |

OTHER PUBLICATIONS

International Search Report of PCT/EP2015/050855, dated Sep. 22, 2015. [PCT/ISA/210].
Written Opinion of PCT/EP2015/050855, dated Sep. 22, 2015. [PCT/ISA/237].
Communication dated Feb. 28, 2019, from the Canadian Intellectual Property Office in corresponding Application No. 2,973,275.
Communication dated Jul. 4, 2019, from the State Intellectual Property Office of the P.R.C in application No. 2015800735903.
Communication dated Jul. 14, 2020, from the Japanese Patent Office in application No. 2019-137416.
Communication dated Jun. 15, 2020, from The China National Intellectual Property Administration in Application No. 201580073590.3.

* cited by examiner

SYSTEM AND METHOD FOR ADJUSTING THE BLOOD GLUCOSE LEVEL OF A PERSON

BACKGROUND OF THE INVENTION

The present invention relates to a system for adjusting the blood glucose level of a person. The invention more particularly relates to a system comprising an insulin delivery device configured to release insulin into the body of a person, as well as an EEG monitor having an EEG sensing part comprising EEG electrodes. The EEG monitor is adapted for being arranged in the ear region of the person with the EEG sensing part arranged subcutaneously at the scalp or arranged in the ear canal. The EEG monitor comprises an EEG signal processor arranged at the ear and adapted for identifying onset of hypoglycemia. The system further comprises a wireless communication link between the EEG monitor and the insulin delivery device.

Insulin delivery devices for continuous insulin infusion, such as insulin pumps, can be arranged to deliver insulin at a rate varying over the day and according to the needs of the person, or, the pump can deliver in response to a specific request made by the person.

There is a wish to combine insulin pumps with a blood glucose monitor, or a continuous glucose monitor (CGM), in order to obtain a continuous automatic control of the blood glucose for a person having diabetes.

A clinical important problem is the lack of possibility to directly control if the person is getting close to a condition of hypoglycemia. It is possible to detect an upcoming onset of hypoglycemia by analysis of the persons EEG.

U.S. Pat. No. 8,348,842 B1 discloses a system comprising an insulin pump and sensors configured to produce an output related to the glycemic state. One type of sensor may be for measuring EEG.

U.S. Pat. No. 6,572,542 B1 discloses a system where a combined processing of electrocardiogram signal and EEG signal is applied for detecting a hypoglycemic event. An event may result in delivery of insulin or glucagon to the patient.

The problem of these known systems is that there is no direct link between the EEG monitoring and the insulin delivery device, and therefore no opportunity for preventing onset of hypoglycemia

SUMMARY OF THE INVENTION

The above problem is solved by a system wherein the EEG monitor is configured to submit a warning signal to the insulin delivery device if an upcoming onset of hypoglycemia is identified by the EEG signal processor. The warning message will cause the insulin delivery device to restrict the insulin delivery for a predetermined time period, and a warning is provided to said person or to a caregiver.

Restriction of the insulin delivery may imply pausing the insulin delivery completely for a predetermined period or, it may imply limiting the insulin delivery to some extend for a predetermined period. The length of the predetermined period as well as the extent to which insulin delivery is limited may depend on the warning message history, e.g. if more warning messages have already been submitted within a relatively short time. Also, the risk of hyperglycemia if the restriction period is too long may be considered.

An advantage of the solution is that an automatic restriction of insulin delivery is provided, thereby improving the safety of the system.

An advantage of the system is that it will allow for a more precise adjustment of the insulin delivery aiming at holding the blood glucose level within an optimum interval. This better adjustment may be achieved by the use of insulin which is more rapid-acting. This can be applied safely due to the extra safety provided by the EEG monitoring. The person applying the system will have the benefit of an improved long term health.

In an embodiment the system also comprises a glucose monitor. This may e.g. be an automatic blood glucose level detector or a continuous glucose monitor (CGM) automatically monitoring the tissue fluid glucose. This makes it possible to evaluate results found from the EEG signal with reference to actual glucose levels. Such a glucose monitor may regularly be calibrated to standard blood glucose measurements.

In an embodiment the insulin delivery device is configured to notify said EEG monitor about a service needed on the insulin delivery device. Such a service could e.g. be the need to recharge or replace battery, to refill the insulin reservoir, or to have some malfunction repaired. The EEG monitor may then notify the user of the system.

In an embodiment the system further comprises a glucagon or glucose delivery device controllable by said EEG monitor. This facilitates that the system may be able to prevent or to remedy a state of hypoglycemia.

In an embodiment the insulin delivery device is configured to deliver insulin only after having controlled that the EEG monitor is functioning and is capturing the EEG signal of the person wearing the system. This prevents that a malfunctioning of the EEG monitor can result in continued delivery of insulin to the person even if there is an upcoming onset of hypoglycemia. In this case a notification should also be given to the person that the EEG monitor is out of function. In practice a malfunctioning EEG monitor may result in that the person is being instructed from the insulin pump to perform a more frequent control of the blood glucose level, and that a minor restriction of the insulin delivery is introduced. I.e. the risk of ending up with hyperglycemia in the effort to avoid hypoglycemia should be avoided.

In an embodiment the EEG monitor comprises an antenna for the wireless communication link, said antenna being adapted for being placed outside the skin layer of the person and outside the ear canal. This position of the antenna facilitates optimum conditions for a reliable electromagnetic communication with the insulin delivery device and other units of the system.

In an embodiment an automatic blood glucose level detector or a CGM is connected to the EEG monitor or to the insulin pump. This facilitates continuous data on the glucose level, which can improve the ability of the system to detect an upcoming onset of hypoglycemia.

In an embodiment the EEG monitor is adapted to send a request to measure the blood glucose level in the event that an upcoming onset of hypoglycemia is identified.

In an embodiment the EEG sensing part is arranged subcutaneously at the scalp. This gives the EEG electrodes a good and reliable contact to the tissue and will give a clear EEG signal.

In an embodiment the EEG monitor comprises a speaker adapted for providing sound messages and alarms from both said EEG monitor and said insulin delivery device to said person. The arrangement of the EEG monitor at the ear region makes a speaker in the EEG monitor easy to hear, without people surrounding the person wearing the system hearing any messages or alarms.

In a second aspect the invention is directed at a method for adjusting the blood glucose level of a person, where the method comprises the steps of provifing an insulin delivery device configured to release insulin into the body of the person;

Arranging an EEG monitor in the ear region of the person, where the EEG monitor has an EEG sensing part comprising EEG electrodes. The EEG sensing part is arranged subcutaneously at the scalp or in the ear canal, and the EEG monitor comprises an EEG signal processor arranged at the ear and adapted for identifying onset of hypoglycemia;

Establishing a wireless communication link between the EEG monitor and the insulin delivery device;

Arranging the EEG signal processor to analyze an EEG signal sampled by the EEG sensing part in order to identify an upcoming onset of hypoglycemia; and Configuring the EEG monitor to submit a warning signal to the insulin delivery device if an upcoming onset of hypoglycemia is identified. The warning message will cause the insulin delivery device to restrict the insulin delivery for a predetermined time period. The EEG monitor further provides a warning to the person or to a caregiver.

BRIEF DESCRIPTION OF THE DRAWINGS

Embodiments of the invention will now be explained in further detail with reference to the figures.

DETAILED DESCRIPTION OF THE INVENTION

Figure 1:
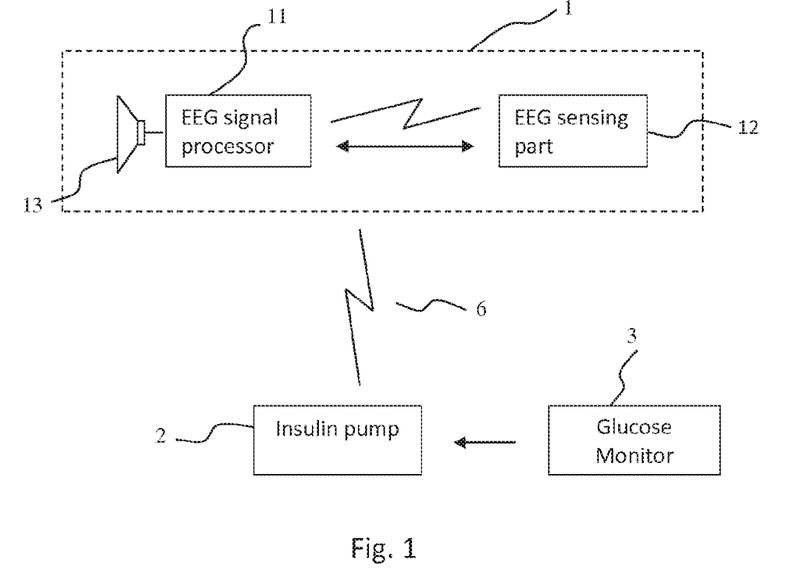
FIG. 1 illustrates a system having an EEG monitor with a sensing part and a signal processor, where the monitor is in communication with an insulin pump, which may receive input from a blood glucose monitor or a CGM.

FIG. 1 shows a system comprising an EEG monitor 1, an insulin delivery device or an insulin pump 2 and a glucose monitor 3 in the form of a blood glucose monitor or a CGM. The EEG monitor 1 and the insulin pump 2 are connected by a wireless connection 6. The glucose monitor 3 may be manual or automatic and has the possibility for entering a measured glucose level into the insulin pump 2.

The EEG monitor 1 is adapted to be arranged in the ear region of the person who is to be monitored. The EEG monitor 1 comprises two main parts: An EEG sensing part 12 and an EEG signal processor 11. Further to this the EEG monitor also comprises a component, e.g. a speaker 13, for providing alarms or messages. The EEG monitor 1 will also comprise a power supply, e.g. in the form of a battery.

The EEG sensing part 12 has electrodes for detecting an EEG signal. The EEG sensing part 12 comprises EEG electrodes which may be arranged subcutaneously at the scalp, preferably in a region extending from behind the ear. The EEG electrodes may also be arranged as surface skin electrodes in the ear canal. The EEG electrodes may be of the type having direct electric connection to the tissue or the skin, or they may be of the capacitive type, where a dielectric material is arranged between the electric conductive part of the electrode and the tissue or skin. The advantages of having the EEG electrodes either subcutaneously or in the ear canal are that good and clear EEG signals can be received, and that the electrodes in these positions will be more protected from picking up electromagnetic noise from the surroundings compared to a position external on the scalp.

The subcutaneous or ear canal positions of the EEG electrodes are preferred also from a cosmetic perspective. The subcutaneous or ear canal positions are furthermore preferred from a reliability point of view since these positions facilitate durable and stable contact to either tissue or skin, i.e. the risk of losing contact, and thereby not being able to detect an EEG signal, is significantly smaller compared to an external electrode which is more likely to lose contact, e.g. during exercise or other daily activities.

The EEG signal processor 11 is adapted to receive the EEG signal from the EEG sensor and to process the signal in order to extract specific features from the measured EEG signal. This feature extraction can be related to e.g. specific frequencies and amplitudes in the EEG signal. Such extracted features may be classified in order to determine if they are relevant to identifying an upcoming onset of hypoglycemia. The EEG signal processor is preferably connected to a speaker in order to provide an alarm of an upcoming onset of hypoglycemia to the user of the system.

A warning signal concerning an identified upcoming onset of hypoglycemia will also be submitted to the insulin pump 2 to which the EEG monitor has a wireless connection 6.

This wireless connection 6 may have any form, but an electromagnetic based or radio connection would often be a preferred choice. The protocol for the connection could be based on Bluetooth, where a low power Bluetooth connection would be preferred.

The insulin pump 2 administers insulin by subcutaneous infusion to the user of the system. The insulin pump typically delivers a continuous basal dose, possibly supplemented with a bolus dose in connection with meals or high blood glucose level. Both basal rate and bolus insulin delivery will be adapted to the needs of the individual user. The input from glucose monitoring is applied in the ongoing adjustment of the insulin dose administered.

Different types of glucose monitors 3 may be applied. One type, the finger stick measurement, is based on obtaining a drop of blood from a small prick in a finger, and placing this on a small strip which is analyzed in a blood glucose meter. The result may be transferred to the insulin pump, either directly e.g. wirelessly, or by the user entering the result to the insulin pump.

An alternative to the direct blood glucose monitoring is, as mentioned, a CGM which measures the glucose level in the tissue fluid. This may include a sensor placed subcutaneously, e.g. by a needle penetrating the skin, where the needle and the spot of penetration are changed with defined intervals. Also, a glucose sensor may be more permanently implanted subcutaneously. Such an implanted glucose sensor is in connection, preferably wirelessly, with an external part which can be a separate part or it can be part of the insulin pump.

When the system of FIG. 1 is in operation, the insulin pump 2 will usually be administering a basal dose supplemented with bolus doses, where the bolus dose may be administered by request of the user. Glucose level is tested at selected times or continuously, and the doses from the insulin pump may be adjusted accordingly. The EEG monitor 1 will monitor the EEG signal continuously, and in the case an upcoming onset of hypoglycemia is detected, a warning signal is sent to the insulin pump and a direct alarm is provided to the user preferably by use of the speaker. If an automatic glucose monitor is part of the system, an alarm from the EEG monitor of an upcoming onset of hypoglycemia should result in the request of a glucose measurement.

If the EEG monitor indicates that onset of hypoglycemia may be upcoming, but the automatic glucose monitor indicates normal glucose level, a manual finger stick type blood glucose measurement could be requested as a control.

The insulin pump is set up to restrict the delivery of insulin to the user when receiving the warning message or signal. Preferably, a physician with insight into the user's diabetes has provided advice, or has decided, on the exact programming of the insulin pump, including programming of the response to any warning signals. Simultaneously with the warning signal to the insulin pump, an alarm is provided to the user. The user should be instructed in advance on how to react to such an alarm, e.g. immediate measurement of the blood glucose level and/or immediate intake of some specific nutrient increasing the blood glucose level.

The exact restriction of the insulin delivery may also depend on the input from a CGM connected to the insulin pump. Depending on the diabetes history of the user it may be that a restriction in insulin delivery is introduced if either the EEG monitor or the CGM measure values indicating that hypoglycemia may be close to onset. It could also be that the level of restriction is determined based on the features in the EEG signal detected by the EEG monitor and on the exact measurement by the CGM. This means that the EEG monitor should submit information related to the features extracted by the EEG signal processor to the insulin pump together with the warning message.

Figure 2:
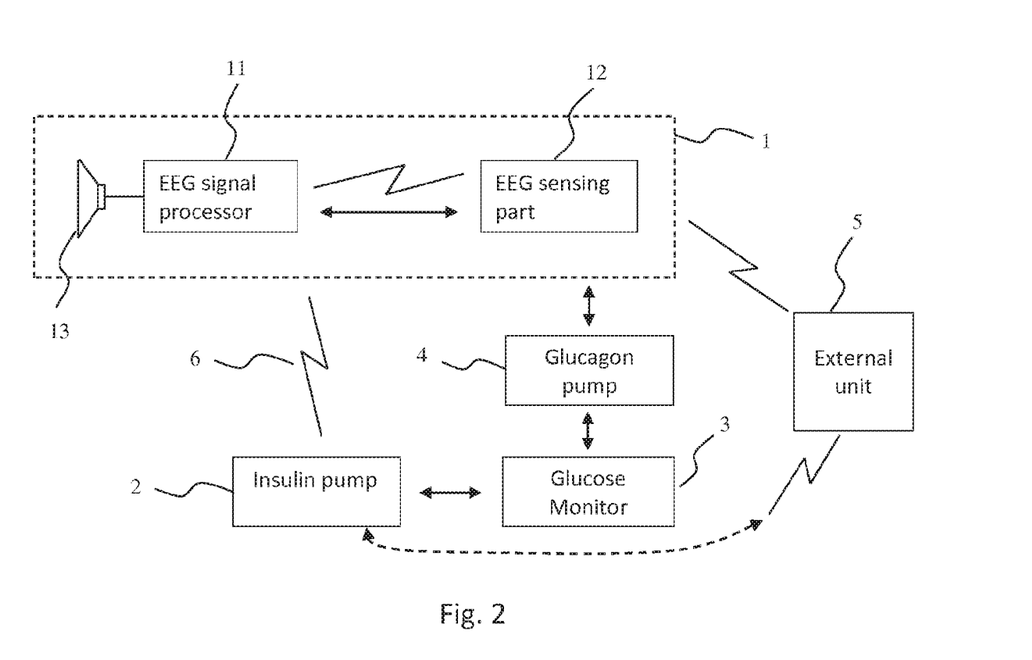
FIG. 2 illustrates the system of FIG. 1 also comprising a Glucagon pump and an external unit.

FIG. 2 shows the system of FIG. 1 to which a glucagon pump 4 has been added. A glucagon pump facilitates that the system may be able to prevent or to overcome an incidence of hypoglycemia. This can be done by having an automatic activation of the glucagon pump resulting in the administration of a glucagon dose, which will increase the blood glucose level. This automatic activation may be triggered if the EEG monitor detects a state of hypoglycemia. A glucagon pump may also be controlled by the person carrying the system. Thereby, the person could administer a glucagon dose in the situation where the EEG monitor submits an alarm on an upcoming onset of hypoglycemia, maybe after having controlled the actual blood glucose level.

Further to the glucagon pump, but independently from this, the system may be provided with an external unit 5. This external unit may have several functions, such as user interface, storing of data, internet connection, and tracking and storing relevant habits of the person carrying the system. Relevant habits may be when the person administers boluses, eats, exercises, or measures the blood glucose manually, which measurement may be entered through the external unit and forwarded to the insulin pump. The external unit may be the person's mobile phone, watch or any small portable computer device, provided with software for the purpose. The connection to one or more components of the system should be wireless, e.g. a Bluetooth connection.

The external unit 5 may thus be applied as interface between the user and the components of the system. The user may enter relevant information such as manually measured blood glucose level, information on meals or anything the user might eat, response to or cancellation of alarms, or any user selected adjustments to the settings of the system.

The external unit 5 may also be applied for presenting information from one or more components of the system to the user. This could be further details in relation to alarms given to the person, e.g. through the speaker. Such details could be instructions on the actions to be taken by the person. Also, information on the operational status of any unit in the system which is connected to the external unit 5 may be provided to the user through the external unit. Examples of this could be battery charging levels or the reservoir levels of the insulin pump or the glucagon pump.

The external unit 5 may also be applied for storage of data. This could be the EEG signal sampled in connection with an event in the EEG signal triggering an alarm. Sampling and collecting the EEG signals related to the triggering of an alarm may be applied for improving the algorithms applied for the extraction of specific features from the EEG signal, and for the classification of those features. Especially, samples of EEG signals in connection with alarms could be applied for adjusting the level or threshold value where an alarm should be provided. For this purpose a measured blood glucose at the time of the alarm will be relevant, and could be sent from an automatic blood glucose monitor or CGM to the external unit 5, or it could be sent from the unit into which the result of a finger stick measurement were entered to the external unit.

The external unit 5 may also have connection to the internet, which may be applied for uploading EEG signal samples directly to a physician, who might also be able to adjust the settings of the system over this internet connection. Alarms may also be forwarded, e.g. to close relatives or helpers, over the internet, or alarms may be transmitted directly to one or more preselected telephone numbers, web-pages or IP-addresses.

Figure 3:
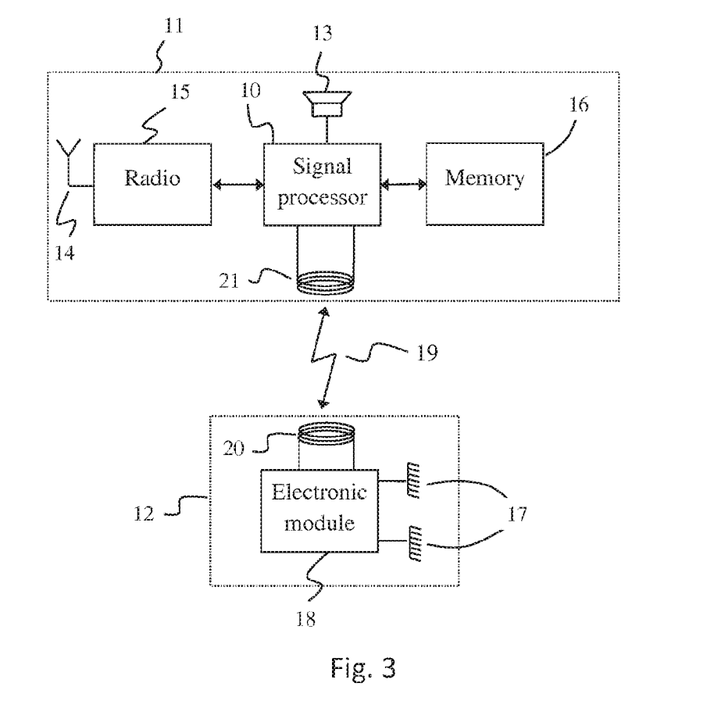
FIG. 3 illustrates the EEG monitor having an EEG sensing part and an EEG signal processor.

FIG. 3 shows an example of the EEG monitor in the system in more details. The EEG monitor 1 comprises an external EEG signal processor 11 and an implantable EEG sensing part 12. The EEG sensing part 12, suitable for being subcutaneously positioned behind the ear of a person, comprises subcutaneous EEG electrodes 17 connected to an electronic module 60. The number of EEG electrodes is at least two. Often at least three electrodes or more are preferred. The electronic module 18, which is shown in more detail in FIG. 4, often comprises an A/D converter 24 and a communication controller 26, and a voltage regulator 27. The electrodes 17 are connected to the A/D converter; the communications controller is connected to a first coil 20 of an inductive link 19.

The EEG signal processor 11 comprises a signal processor 10 having a controller (not shown) connected to a second coil 21 of the inductive link 19. The signal processor 10 is further connected to a battery (not shown) for power supply and to a loudspeaker 13 for providing an acoustic signal, e.g. an alarm in the event that an upcoming onset of hypoglycemia is identified. The EEG signal processor part 11 also comprises a memory 16, e.g. for logging of data, as well as a radio 15 with an antenna 14, for wireless communication with other units in the system, and e.g. with the external unit.

When in use, the EEG signal processor 11 may be placed behind the ear of a person for whom monitoring of an EEG signal is desired, and in the vicinity of a subcutaneously implantable EEG sensing part 12, which preferably is implanted right below the skin and slightly behind the ear of the user and positioned in such a way that a reliable, electrical EEG signal may be detected by the electrodes 17.

Figure 4:
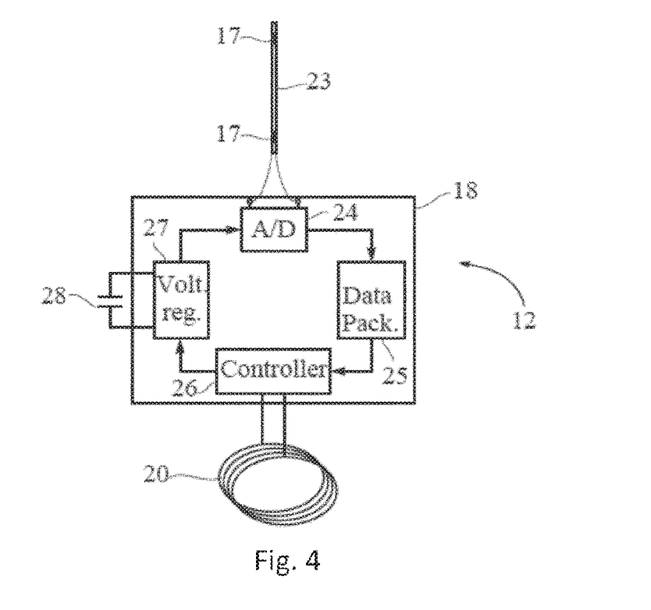
FIG. 4 illustrates an example of an EEG sensing part.

As illustrated in more details in FIG. 4 the electrodes 17 of the EEG sensing part 12 can be arranged in one wire 23 having the electrodes 17 arranged with contact to the tissue in limited areas along the wire 23.

The electrodes 17 pick up EEG signals as a varying electrical voltage potential and feed the varying electrical voltage to the A/D converter 24 in the electronic module 18. The A/D converter 24 converts the varying electrical voltage into a digital signal and presents this digital signal to a data packet controller 25 which is part of the electronic module 18. The data packet controller 25 arranges the digital signal into a stream of data packets according to a predetermined communications protocol, and feeds the resulting stream of data packets to the communications controller 26.

The communications controller 26 is configured to energize the electronic module 18 electromagnetically by receiving energy from the second coil 21 of the external EEG signal processor 11 by the first coil 20. The electromagnetic energy received in the first coil 20 is transferred to the voltage regulator 27 which, together with a ceramic capacitor 28, is applied as a power source for the electronic module 18.

Furthermore, the communications controller 26 takes data packets representing the EEG signals from the electrodes 17 and transfers this digitized EEG signal from the EEG sensing part through the inductive link by modulating the load on the power received in the first coil 20 from the second coil 21. This modulated load is detectable from the EEG signal processor 11, where the modulation of the load is converted into an electrical signal suitable for being continuously decoded and analyzed by the signal processor 10.

The analysis of the EEG signal in order to identify an upcoming onset of hypoglycemia may be based on different algorithms. One example on how this analysis can be performed is given in WO 2012/069549 A1.

Depending on the results of the analysis of the EEG signals, decisions may be taken by the signal processor 10 to activate the loudspeaker 13 sounding an alarm if upcoming onset of hypoglycemia is identified.

The EEG electrodes 17 in the embodiment shown in FIG. 3 are arranged to be implanted subcutaneously behind the ear of a user in order to provide a signal suitable for detection by the electronic module of the EEG sensing part 12. A typical output signal from the EEG electrode has a magnitude in the range of approximately 1 µV to 100 µV. Muscular contractions usually generate voltage levels of a magnitude of 10 mV, but such signals are filtered out by the system. The intrinsic noise level of the electrode is about 1 µV RMS measured over a bandwidth from 0.1 to 100 Hz, and the useable bandwidth of the output signal is 0.1 to 40 Hz.

The EEG sensing part 12 is encased in a bio-compatible material (not shown), such as a ceramic. The electrodes are also made from a bio-compatible metal, such as a platinum-iridium alloy. When the EEG signal processor 11 is worn behind the ear (as a behind-the-ear hearing aid) where the implant has been positioned, the second coil 21 of the EEG signal processor 11 will be a few millimeters from the first coil 20 of the EEG sensing part 12. This facilitates communication and transfer of power between the EEG signal processor 11 and the EEG sensing part 12. The two coils should preferably be closely aligned, whereby a more efficient transfer of power and a more reliable communication can be achieved.

The EEG sensing part of the EEG monitor is described as implantable in relation to FIGS. 3 and 4. However, the EEG sensing part can also be arranged in the ear canal with the electrodes detecting the EEG signal from the skin surface of the ear canal. An example of an ear plug with electrodes for this purpose is given in WO 2011/000383 A1 (see e.g. FIG. 2 of this publication)

Figure 5:
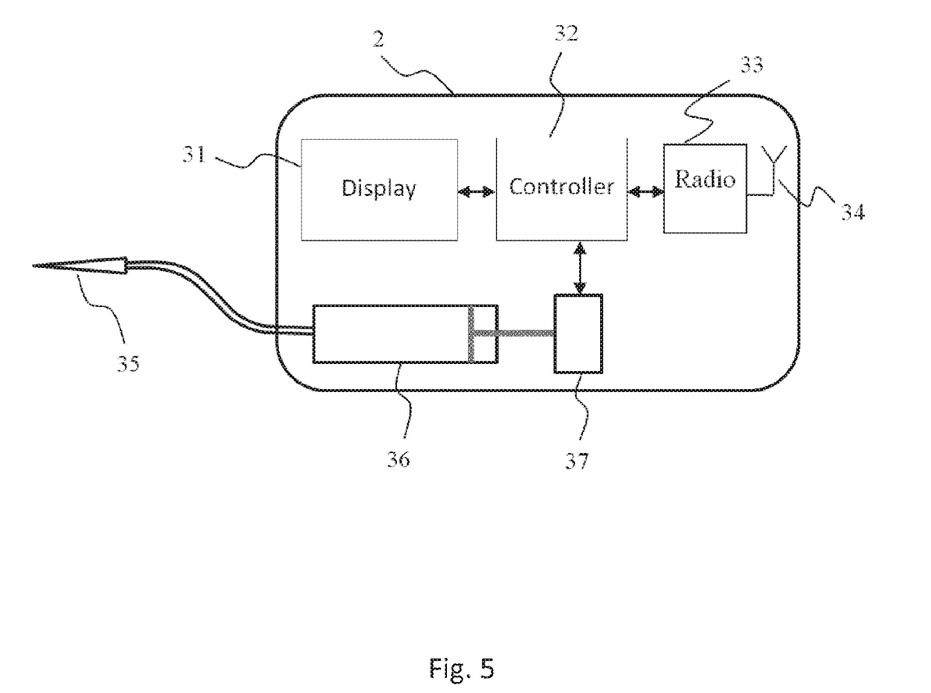
FIG. 5 illustrates an example of an insulin pump.

FIG. 5 shows an example of an insulin pump 2 for the system. The insulin pump has display 31 for communication with the user, and a controller 32 for controlling the delivery of insulin to the person wearing the insulin pump. The insulin pump also comprises a radio 33 with an antenna 34 for the communication with other units of the system. Further the insulin pump comprises a reservoir 36 for insulin and a motor 37 for moving a piston in order to deliver insulin through an infusion set comprising a cannula 35.

The wireless connection between the EEG monitor and the insulin pump should have a protocol ensuring a high degree of reliability in the communication. The protocol should confirm that there is a connection at regular time intervals, e.g. once a second, and if connection has been lost for more than e.g. 15 seconds a notification may be provided to the person wearing the system or to a caregiver. In the situation where the wireless connection is lost, both the insulin pump and the EEG monitor should continue functioning according to their programmed settings. In that case the person using the system should be clearly notified, and a caregiver might be notified as well. In case the EEG monitor detects an upcoming onset of hypoglycemia in this situation where the wireless connection is lost, the warning provided to the person and/or caregiver should clearly emphasize that no automatic restriction (e.g. pause or limitation) of the insulin delivered from the insulin pump can be performed.

If the connection between insulin pump and EEG monitor is lost, any action the insulin pump is programmed to take should depend on the availability of automatic and continuous blood glucose measurements or a CGM. One option is that bolus doses are only delivered after notification and confirmation by the user. Also, if the system comprises a glucagon pump to which the EEG monitor continues to have a fully functional connection, such a glucagon pump would offer safety, if the EEG monitor is able to control the delivery of glucagon in case an upcoming onset of hypoglycemia is identified. Any such programming should be based on the individual user's needs, and should therefore be based on consultation with a physician knowing the diabetic status of the person.

Speech messages or notifications from any device in the system may be provided to the person using the system through the EEG monitor. This could include information from the insulin pump that the insulin reservoir has reached a level where a refill is advisable, or that the batteries in the insulin pump needs recharging or replacement. For safety reasons it is preferred that the insulin pump has a separate alarm means in order to provide alarms also if the wireless connection between the EEG monitor and the insulin pump should be lost.

The invention claimed is:

1. A system for adjusting the blood glucose level of a person, comprising
    an EEG monitor comprising an EEG signal processor adapted for being arranged at an ear of the person and adapted for identifying onset of hypoglycemia,
    a glucose monitor,
    an insulin delivery device configured to release insulin into the body of said person responsive to outputs from at least one of said EEG monitor and glucose monitor, and
    a first communications connection between said EEG monitor and said insulin delivery device,
    wherein said system is configured to operate said insulin delivery device in accordance with an output from said EEG monitor when said first communications connection is present, and in accordance with an output from said glucose monitor in response to said connection between said EEG monitor and insulin delivery device being lost.

2. The system according to claim 1, wherein said insulin delivery device is configured to notify said EEG monitor about a service needed on the insulin delivery device.

3. The system according to claim 1, wherein said system further comprises a glucagon or glucose delivery device controllable by said EEG monitor.

4. The system according to claim 1, wherein said insulin delivery device is configured to deliver insulin only after having ascertained that said EEG monitor is functioning and is capturing the EEG signal of said person.

5. The system according to claim 1, wherein said EEG monitor comprises an antenna for said communications connection, said antenna being adapted for being placed outside the skin layer and outside the ear canal.

6. The system according to claim 1, wherein said glucose monitor is automatic, and is connected to said EEG monitor or to said insulin pump.

7. A system for adjusting the blood glucose level of a person, comprising
an insulin delivery device configured to release insulin into the body of said person,
an EEG monitor comprising an EEG signal processor adapted for identifying onset of hypoglycemia, and
a communications connection between said EEG monitor and said insulin delivery device,
wherein said EEG monitor is adapted to send a request to measure the glucose level by a method other than EEG analysis in response to an upcoming onset of hypoglycemia being identified by said EEG signal processor.

8. The system according to claim 1, wherein said EEG monitor comprises an EEG sensor part adapted for being arranged subcutaneously at the scalp.

9. The system according to claim 1, wherein said EEG monitor comprises a speaker adapted for providing sound messages and alarms from both said EEG monitor and from said insulin delivery device to said person.

10. A method for adjusting the blood glucose level of a person, said method comprising the steps of
providing an insulin delivery device configured to release insulin into the body of said person,
arranging an EEG monitor comprising an EEG signal processor arranged at an ear of said person and adapted for identifying onset of hypoglycemia,
establishing a first communications connection between said EEG monitor and said insulin delivery device,
configuring said EEG monitor to
send a request to measure the glucose level by a method other than EEG analysis in response to an upcoming onset of hypoglycemia being identified by said EEG signal processor.

11. The system according to claim 1,
wherein said EEG monitor is configured to submit a warning signal to said insulin delivery device if an upcoming onset of hypoglycemia is identified by said EEG signal processor, said warning signal causing said insulin delivery device to restrict the insulin delivery for a predetermined time period commencing with said identification of an upcoming onset of hypoglycemia, and wherein a warning is provided to said person or to a caregiver; and
wherein the duration of said predetermined time period is determined based at least in part on a past history of alarms.

12. The system according to claim 1,
wherein said EEG monitor is configured to submit a warning signal to said insulin delivery device if an upcoming onset of hypoglycemia is identified by said EEG signal processor, said warning signal causing said insulin delivery device to restrict the insulin delivery for a predetermined time period commencing with said identification of an upcoming onset of hypoglycemia, and wherein a warning is provided to said person or to a caregiver; and
wherein said step of restricting insulin delivery comprises permitting insulin delivery during said predetermined time period but at a reduced level.

13. The method according to claim 10,
wherein said EEG monitor is configured to submit a warning signal to said insulin delivery device in response to identification of an upcoming onset of hypoglycemia by said EEG signal processor, said warning signal causing said insulin delivery device to restrict the insulin delivery for a predetermined time period commencing with said identification of an upcoming onset of hypoglycemia, and wherein a warning is provided to said person or to a caregiver; and
wherein the duration of said predetermined time period is determined based at least in part on past history of alarms.

14. The method according to claim 10,
wherein said EEG monitor is configured to submit a warning signal to said insulin delivery device in response to identification of an upcoming onset of hypoglycemia, said warning signal causing said insulin delivery device to restrict the insulin delivery for a predetermined time period commencing with said identification of an upcoming onset of hypoglycemia, and
wherein said step of restricting insulin delivery comprises permitting insulin delivery during said predetermined time period but at a reduced level.

15. The system according to claim 1, wherein insulin delivery is automatically limited to a restricted level in the case of a malfunctioning EEG monitor.

16. The method according to claim 10, wherein insulin delivery is automatically limited to a restricted level in the case of a malfunctioning EEG monitor.

17. A system for adjusting the blood glucose level of a person, comprising
an EEG monitor comprising an EEG signal processor arranged at an ear of the person and adapted for identifying onset of hypoglycemia,
a glucose monitor for monitoring a glucose level of said person,
an insulin delivery device configured to release insulin into the body of said person responsive to outputs from at least one of said EEG monitor and glucose monitor, and
a communications connection between said EEG monitor and said insulin delivery device,
wherein said EEG monitor is configured to submit a warning signal to said insulin delivery device if an upcoming onset of hypoglycemia is identified by said EEG signal processor, and
wherein said system is configured to adjust at least one threshold level at which said EEG monitor provides said warning signal based at least in part on glucose measurements from said glucose monitor.

18. The method according to claim 10, wherein said method further comprises the step of operating said insulin pump in accordance with an output from a glucose monitor in response to the connection between said EEG monitor and insulin pump being lost.

19. The method according to claim 10,
wherein said EEG monitor is configured to submit a warning signal to said insulin delivery device in response to identification of an upcoming onset of hypoglycemia, and
wherein said method further comprises the step of adjusting at least one threshold level at which said EEG monitor provides said warning signal based at least in part on glucose measurements from said glucose monitor.

20. The system according to claim 1, wherein insulin delivery is operated in a closed loop control manner in accordance with said output from said EEG monitor when said first communications connection is present, and is operated in a closed loop control manner in accordance with said output from said glucose monitor when said first communications connection is lost.

21. The system according to claim 1, wherein said insulin delivery is operated in accordance with said output from said EEG monitor when said first communications connection is present, and wherein said output from said glucose monitor is provided to said insulin delivery device while said connection is lost, over a second communications connection different from said first communications connection.

\* \* \* \* \*